US005710114A

United States Patent [19]

Pyles

[11] Patent Number: 5,710,114
[45] Date of Patent: Jan. 20, 1998

[54] STABLE CONDITIONING SHAMPOO CONTAINING AN ANIONIC SURFACTANT, A FATTY ALCOHOL, AND POLYETHYLENEIMINE

[75] Inventor: Daniel Raymond Pyles, Chicago, Ill.

[73] Assignee: Helene Curtis, Inc., Chicago, Ill.

[21] Appl. No.: 654,864

[22] Filed: May 29, 1996

Related U.S. Application Data

[63] Continuation of Ser. No. 538,249, Oct. 3, 1995, Pat. No. 5,576,279, which is a continuation-in-part of Ser. No. 305,069, Sep. 13, 1994, abandoned, which is a continuation-in-part of Ser. No. 63,015, May 17, 1993, abandoned.

[51] Int. Cl.$^6$ .................... A61K 7/075; C11D 1/62; C11D 1/65; C11D 3/37

[52] U.S. Cl. .......... 510/123; 424/70.122; 424/70.22; 510/122; 510/125; 510/127; 510/437; 510/475; 510/504; 510/505

[58] Field of Search .............................. 510/122, 127, 510/415, 119, 123, 124, 125, 437, 504, 505; 424/70.122, 70.22, 70.11, 70.17, 70.24

[56] References Cited

U.S. PATENT DOCUMENTS

| | | | |
|---|---|---|---|
| 3,400,198 | 9/1968 | Lang | 424/70.17 |
| 3,761,417 | 9/1973 | Parran, Jr. | 510/382 |
| 3,870,660 | 3/1975 | Paviak | 132/202 |
| 4,777,039 | 10/1988 | Lang et al. | 424/70.28 |
| 4,859,457 | 8/1989 | Suzuki et al. | 424/70.122 |
| 4,997,641 | 3/1991 | Hartnett et al. | 424/70.122 |
| 5,019,376 | 5/1991 | Uick | 424/70.28 |
| 5,034,218 | 7/1991 | Duvel | 424/70.12 |
| 5,047,177 | 9/1991 | Varco | 510/121 |
| 5,051,250 | 9/1991 | Patel et al. | 424/70.19 |
| 5,104,645 | 4/1992 | Cardin et al. | 514/345 |
| 5,114,706 | 5/1992 | Duvel | 424/70.17 |
| 5,213,716 | 5/1993 | Patel et al. | 510/122 |
| 5,213,792 | 5/1993 | Grundmann et al. | 424/70.28 |
| 5,221,530 | 6/1993 | Janchitraponvej et al. | 424/70.11 |
| 5,248,445 | 9/1993 | Rizvi et al. | 510/122 |
| 5,346,642 | 9/1994 | Patel et al. | 510/122 |
| 5,360,581 | 11/1994 | Rizvi et al. | 510/122 |
| 5,417,965 | 5/1995 | Janchitraponvej et al. | 510/122 |
| 5,556,616 | 9/1996 | Janchitraponvej et al. | 424/70.122 |
| 5,576,279 | 11/1996 | Pyles | 510/122 |
| 5,580,494 | 12/1996 | Sandhu et al. | 510/125 |

*Primary Examiner*—Ardith Hertzog
*Attorney, Agent, or Firm*—Matthew Boxer

[57] ABSTRACT

A conditioning shampoo containing an anionic surfactant, a long-chain fatty alcohol, and a cationic polyethyleneimine, has extended product stability, excellent cleansing and foaming properties, and provides excellent and improved overall conditioning to human hair, particularly superior wet and dry combing properties.

15 Claims, No Drawings

5,710,114

STABLE CONDITIONING SHAMPOO CONTAINING AN ANIONIC SURFACTANT, A FATTY ALCOHOL, AND POLYETHYLENEIMINE

CROSS-REFERENCE TO RELATED APPLICATIONS

This application is a continuation of U.S. patent application Ser. No. 08/538,249, filed Oct. 3, 1995, now U.S. Pat. No. 5,576,279, which is a continuation-in-part application of U.S. patent application Ser. No. 08/305,069, filed Sep. 13, 1994, abandoned, which is a continuation-in-part application of U.S. patent application Ser. No. 08/063,015, filed May 17, 1993, abandoned.

FIELD OF INVENTION

The present invention is directed to a hair conditioning shampoo composition and to a method of treating hair with the composition to cleanse the hair and, at the same time, to provide the hair with improved wet-stage and dry-stage conditioning properties as well as other conditioning properties, such as softness, without residual buildup of conditioning agents on the hair. More particularly, the present invention is directed to a hair conditioning shampoo composition including one or more anionic cleaning surfactants, such as ammonium lauryl sulfate; a cationic (protonated) polyethyleneimine; and, in the preferred embodiment, a long-chain fatty alcohol that provides lauryl ($C_{12}$) alcohol in the composition in an amount of at least about 75% by weight, based on the weight of polyethyleneimine in the composition. Surprisingly, the combination of one or more long-chain ($C_8$–$C_{18}$) fatty alcohols, predominantly $C_{12}$ fatty alcohol, preferably at least 75% by weight lauryl alcohol, based on the weight of the cationic polyethyleneimine in the composition, and a cationic polyethyleneimine, effectively increases foam volume and conditioning properties while maintaining excellent cleansing in a composition that is stable over extended periods of time at elevated temperatures.

BACKGROUND OF THE INVENTION AND PRIOR ART

Soiled human hair is shampooed to remove sebum that is naturally secreted by the head, as well as soil and other atmospheric contaminants that accumulate on the hair. Sebum, in particular, accumulates on the hair in a relatively short period of time leaving the hair with a greasy, dirty feel and poor manageability. The most effective shampoos for cleansing the hair for removal of the atmospheric contaminants and sebum are those that contain high lather synthetic anionic detergents, such as the long-chain alkyl sulfates and the partially ethoxylated long-chain alkyl sulfates. These synthetic anionic detergents are very effective for cleansing the hair but, after rinsing with water, leave the hair with a dried touch, usually called "creak" and result in hair, when wet, that is in an extremely tangled and unmanageable after-shampoo condition.

Thoroughly cleansed hair is extremely difficult to comb in either the wet or dry state because the individual hair fibers tend to snarl, kink, and interlock with each other. Particularly prior to complete drying of thoroughly cleansed hair in this after-shampoo stage the hair is very difficult to comb or brush. Even after complete drying, the thoroughly cleansed hair remains difficult to comb or brush and does not set well. Thoroughly clean, dried hair also has undesirable electrostatic properties in a low humidity atmosphere that causes the hair to "fly away," thereby further reducing the combing or brushing property of the hair. Generally, these above-outlined problems that result from synthetic detergent cleansing of the hair, particularly the high-lather synthetic anionic detergents, have been elevated either by the after-shampoo treatment of the hair with hair conditioners, for example in the form of a hair rinse, or by including hair conditioners directly within the shampoo composition.

After-shampoo hair conditioning compositions are easily formulated but are inconvenient to use because of the necessity of applying the conditioner to the hair in a separate stage after shampooing. The preparation of a conditioning shampoo has been more difficult because of inherent incompatibility problems between anionic surfactants and the fatty cationic compounds that are good conditioning agents. Contact between an anionic surfactant and a cationic surfactant or cationic polymer produces a precipitate that forms immediately or causes an interaction between the anionic and cationic compounds that significantly reduces their respective cleaning and conditioning properties. The reduction in cleansing and conditioning effectiveness is observed even in compositions wherein the anionic and cationic compounds do not precipitate from the composition but remain in solution or suspension. This incompatibility between an anionic surfactant and a cationic conditioning compound is well recognized by those skilled in the art. For example, Safarin in *Cosmetics*, Interscience Publishers, Inc., New York, p. 538 (1957), states that anionic and cationic compounds cannot be used in combination because they react to form insoluble salts.

A partial solution to this incompatibility problem in the formulation of conditioning shampoos is exemplified by the following patents that disclose compositions that contain surfactants that are not anionic, e.g., nonionics, amphoterics and zwitterionics, together with cationic conditioning compounds: U.S. Pat. No. 3,849,348 to Hewitt; U.S. Pat. No. 3,990,991 to Gerstein; and U.S. Pat. No. 3,822,312 to Sato. Published European Patent Application EP 0 407 042 A2 teaches long chain alcohols, long chain ethoxylated alcohols and/or long chain esters or acids in conditioning shampoos.

The compositions of the present invention are stable and have increased foam volume and conditioning properties without amine oxide or acyl derivative suspending agents.

SUMMARY OF THE INVENTION

In accordance with the principles of the present invention, it has been found, surprisingly, that a conditioning shampoo composition containing an anionic surfactant; a cationic polyethyleneimine; and a long-chain fatty alcohol, preferably at least 75% by weight $C_{12}$ fatty alcohol, based on the weight of polyethyleneimine, has extended product stability, excellent cleansing and foaming properties, and provides excellent and improved overall conditioning to human hair, particularly superior wet and dry combing properties.

Hair treated with the composition of the present invention is thoroughly cleansed with increased foam and exhibits improved physical and cosmetic properties, such as gloss, thickness, manageability, softness and body. Further, it was surprisingly and unexpectedly found that hair treated with the composition of the present invention does not experience buildup on the hair shaft, over time, of conditioning agents, as is common with many conditioning shampoo compositions.

Therefore, an aspect of the present invention is to provide a hair-treating composition that cleanses the hair, provides improved foam volume, and imparts improved physical properties and cosmetic properties to the hair in a single application.

Another aspect of the present invention is to provide a physically stable conditioning shampoo composition containing an anionic surfactant, a cationic (protonated) polyethyleneimine polymer and a fatty $C_8$–$C_{18}$ alcohol, wherein the composition includes lauryl ($C_{12}$) alcohol in an amount of at least 75% by weight, based on the weight of polyethyleneimine in the composition.

Another aspect of the present invention is to provide a new and improved conditioning shampoo composition containing a strong anionic detergent, such as a long-chain alkyl sulfate, long-chain alkyl ether sulfate, and/or long-chain sulfonate; a cationic polyethyleneimine, and a long-chain ($C_8$–$C_{18}$) fatty alcohol, wherein the fatty alcohol includes $C_8$, $C_{10}$, $C_{14}$, $C_{16}$ and/or $C_{18}$ fatty alcohol in a fatty alcohol:polyethyleneimine weight ratio of at least 2.67:1, having improved foaming, conditioning, and stability.

Still another aspect of the present invention is to provide a new and improved conditioning shampoo including about 5% to about 65% of an anionic surfactant; about 0.5% to about 10% of a long-chain (predominantly $C_8$–$C_{18}$) fatty alcohol, containing sufficient $C_{12}$ fatty alcohol to provide at least 75% by weight lauryl alcohol, based on the weight of PEI in the composition; and about 0.01% to about 4%, preferably about 0.01% to about 1%, cationic (protonated) polyethyleneimine.

A further aspect of the present invention is to provide a new and improved method of making an aqueous conditioning shampoo having an anionic surfactant, a cationic polyethyleneimine, and a fatty alcohol that includes sufficient $C_{12}$ fatty alcohol such that the composition includes at least about 75% by weight $C_{12}$ (lauryl) alcohol based on the weight of PEI in the composition, by vigorously mixing the composition to provide new and unexpected stability to the conditioning shampoo composition.

Still another aspect of the present invention is to provide a new and improved conditioning shampoo composition having a pH in the range of about 2 to about 8, preferably about 4 to about 7, and more preferably about 5 to about 6 including about 5% to about 65% of an anionic surfactant; a cationic (protonated) polyethyleneimine in an amount of about 0.01% to about 4% by weight, preferably about 0.01% to about 2% by weight, more preferably about 0.1% to about 1% by weight; about 0.5% to about 10% lauryl alcohol, wherein the lauryl alcohol is included in the composition in an amount of at least about 75% by weight, based on the weight of PEI in the composition, and optionally, about 0.1% to about 20% of a cationic, nitrogen-containing conditioning agent having only two long-chain alkyl radicals bonded to the nitrogen atom, the long-chain radicals having predominantly about 12 to about 22 carbon atoms per long-chain alkyl radical.

Another aspect of the present invention is to provide a new and improved conditioning shampoo having a pH in the range of about 4 to about 7, preferably about 5 to about 6, including about 5% to about 65% of an anionic surfactant; a cationic protonated polyethyleneimine in an amount of about 0.01% to about 4%, preferably about 0.01% to about 1% by weight, and having a cationic polymer charge density of at least about 10 milliequivalents per gram; preferably about 15 to about 20 milliequivalents per gram; and about 0.5% to about 10% of a long-chain ($C_8$–$C_{18}$) fatty alcohol, wherein at least about 75% by weight $C_{12}$ (lauryl) alcohol is included in the composition, based on the weight of PEI in the composition and, optionally, about 0.1% to about 20% of a cationic, nitrogen-containing conditioning agent having only two long-chain alkyl radicals bonded to the nitrogen atom, the long-chain radicals having predominantly about 12 to about 22 carbon atoms per long-chain alkyl radical.

The above and other aspects and advantages of the present invention will become apparent from the following detailed description of the preferred embodiments.

DETAILED DESCRIPTION OF THE PREFERRED EMBODIMENTS

The aqueous conditioning shampoo composition of the present invention generally includes an anionic surfactant in an amount of about 5% to about 65%, preferably about 5% to about 25%, by weight of the composition; about 0.01% to about 4% by weight of a cationic polyethyleneimine; and one or more water-insoluble long chain ($C_8$–$C_{18}$) fatty alcohols in an amount of about 0.5% to about 20% by weight of the composition, wherein the amount of lauryl alcohol is at least 75% by weight, based on the weight of cationic polyethyleneimine in the composition.

The conditioning shampoo of the present invention provides the hair with improved foam, as well as improved physical and cosmetic conditioning properties, such as gloss, thickness, softness, and manageability, including excellent wet and dry combing properties and body. The composition of the present invention remains stable, while achieving excellent cleansing, foaming, and conditioning.

The anionic cleansing surfactant used in the composition and method of the present invention can be any of the anionic surfactants known or previously used in the art of hair shampoos. An anionic cleansing surfactant should be included in the composition of the present invention to effectively cleanse the hair and generates a high, stable foam level that consumers equate with cleaning efficiency. Nonionic and amphoteric surfactants are not as effective in cleansing the hair and do not provide the high foam level desired by consumers. However, optionally, nonionic, amphoteric, and/or zwitterionic surfactants can be included in the compositions of the present invention in addition to one or more anionic surfactants to help stabilize foam, to provide a suitable viscosity, or to give other functional or esthetic properties to the composition.

Usually, the anionic cleansing surfactant includes a hydrophobic moiety, such as a carbon chain including from about 8 carbon atoms to about 30 carbon atoms, and particularly from about 12 carbon atoms to about 20 carbon atoms, and further includes a hydrophilic moiety, such as a sulfate, sulfonate, carbonate, phosphate, or carboxylate. Often, the hydrophobic carbon chain is etherified, such as with ethylene oxide or propylene oxide, to impart a particular physical property, such as increased water-solubility or reduced surface tension, to the anionic cleansing surfactant.

Suitable anionic cleansing surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, alkyl ether carboxylates, fatty acids, succinamates, sulfosuccinates, sarcosinates, octoxynol or nonoxynol phosphates, taurates, fatty taurides, sulfated monoglycerides, fatty acid amino polyoxyethylene sulfates, and isothienates, or combinations thereof. Many additional anionic cleansing surfactants are described in McCUTCHEON'S DETERGENTS AND EMULSIFIERS, 1989 ANNUAL, published by McCutcheon's Division MC Publishing Company, herein incorporated by reference. Usually, the anionic cleansing surfactant is present in the composition as a neutralized salt in the form of a sodium, potassium, lithium, ammonium, alkylammonium, or hydroxyalkylammonium salt, wherein the alkyl moiety includes from 1 to about 3 carbon atoms. The alkyl sulfates and alkyl ether sulfates are particularly effective classes of anionic cleansing surfactants. Exemplary anionic cleansing surfactants that are useful in the composition and method of the present invention include, but are not limited to, the ammonium, monoethanolamine, diethanolamine, triethanolamine, isopropylamine, sodium, potassium, lithium, or magnesium salts of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide, or combinations thereof. An especially useful anionic cleansing surfactant is a mixture of a lauryl sulfate salt and a lauryl ether sulfate salt.

The conditioning shampoos of the present invention achieve excellent conditioning, foaming, and stability without the aryl derivatives or amine oxides disclosed to be necessary for stability in Grote U.S. Pat. No. 4,741,855. The ability to provide a conditioning shampoo that has excellent conditioning benefits, as well as excellent foaming and stability, has been a long-felt need in the conditioning shampoo art. The conditioning shampoos of the present invention solve this long-felt need by including a cationic polyethyleneimine in combination with a long-chain fatty alcohol, including lauryl alcohol in an amount of at least 75% by weight, based on the weight of polyethyleneimine, to stabilize the suspension of silicone and other water-insoluble conditioning agents without substantially decreasing the foaming or conditioning benefits.

Surprisingly, protonated polyethyleneimine (PEI), together with the long chain alcohol ($C_8$–$C_{18}$), including lauryl alcohol in an amount of at least 75% by weight, based on the weight of polyethyleneimine, provides excellent stability while achieving additional conditioning benefits from the protonated polyethyleneimine. It should be understood that the polyethyleneimine can be added to the composition of the present invention in the protonated form, or can be protonated in situ (after addition to the composition) by an acid that is in the composition for pH control, and PEI protonation if needed. The molecular weight of the polyethyleneimine is not critical and can be any molecular weight commercially available, e.g., protonated polyethyleneimines available from BASF Corporation having a weight average molecular weight in the range of about 700 to about 1,000,000. The higher molecular weight PEI's, e.g., about 50,000 to about 1,000,000 weight average molecular weight, are preferred. The ability to provide a conditioning shampoo that has excellent conditioning benefits, as well as excellent foaming and stability, has been a long-felt need in the conditioning shampoo art. The conditioning shampoos of the present invention solve this long-felt need by including a protonated polyethyleneimine and a long-chain ($C_8$–$C_{18}$) fatty alcohol, including lauryl alcohol in an amount of at least about 75% by weight, based on the weight of polyethyleneimine. The structure of the protonated polyethyleneimine is as follows:

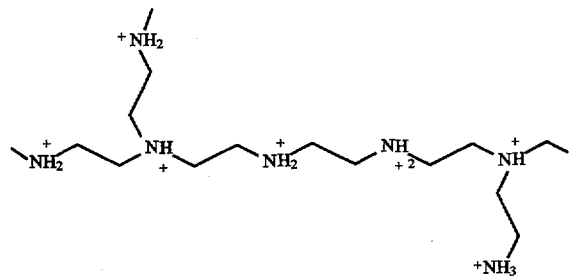

The preferred protonated polyethyleneimines have a ratio of primary: secondary: tertiary nitrogen atoms of about 1:2:1, respectively.

The fatty alcohol provides good stability to a shampoo composition containing cationic polyethyleneimine, while unexpectedly maintaining foaming and conditioning benefits. In accordance with a preferred embodiment of the present invention, the fatty alcohol has a chain-length distribution primarily in the $C_8$–$C_{18}$ range, which includes sufficient lauryl alcohol such that the composition contains at least 75% by weight lauryl alcohol, based on the weight of polyethyleneimine in the composition. The fatty alcohols can include ethoxylated fatty alcohols, in the $C_8$–$C_{18}$ range, preferably $C_{12}$–$C_{16}$ range, and in the preferred embodiment, should include lauryl alcohol or ethoxylated lauryl alcohol, in an amount of at least 75% by weight, based on the weight of polyethyleneimine. Such shampoo compositions have been found to maintain exceptional foaming and provide excellent stability while maintaining the conditioning benefits of the PEI with or without one or more suspended, water-insoluble conditioning agents, such as a silicone conditioning agent.

Foam boosters can be added to the compositions of the present invention to further increase the foam volume attributed by the anionic and other detergents. Suitable foam boosters include, for example, polyvinylpyrrolidone (PVP); polyox; cetyl betaine; cocamide; cocamidoethyl betaine; cocamidopropyl betaine; cocamidopropyl hydroxysultaine; cocoamphodipropionic acid; coco-betaine; coco/oleamidopropyl betaine; coco-sultaine; cocoyl hydroxyethyl imidazoline; DEA-cocoamphodipropionate; DEA-lauraminopropionate; decyl betaine; disodium isostearyl sulfosuccinate; isopropyl stearate; lauramide; lauramidopropyl betaine; lauryl betaine; lauryl sultaine; myristamidopropyl betaine; myristaminopropionic acid; myristyl betaine; oleamidopropyl betaine; oleamidopropyl hydroxysultaine; oleyl betaine; palmamidopropyl betaine; palmitamidopropyl betaine; PEG-6 cocamide; PEG-3 lauramide; PEG-5 lauramide; PEG-6 lauramide; sodium cocoamphoacetate; sodium cocoamphopropionate; sodium lauraminopropionate; sodium lauroamphopropionate; sodium lauroyl sarcosinate; sodium myristoamphoacetate; sodium myristoyl sarcosinate; TEA-hydrogenated tallow glutamate; TEA-lauraminopropionate; TEA-myristaminopropionate; and undecylenamidopropylamine oxide.

To achieve the full advantage of the present invention, an optional nonionic alkanolamide is included in the conditioning shampoo composition in an amount of about 0.1% to about 5% by weight to provide exceptionally stable emulsification of water-insoluble conditioning agents and to aid in thickening and foam stability. Other useful suspending and thickening agents can be used instead of the alkanolamides, such as sodium alginate, guar gum, xanthan gum, gum arabic, cellulose derivatives, such as methylcellulose, hydroxybutylcellulose, hydroxyethylcellulose, hydroxypropylcellulose, and carboxymethylcellulose, and various synthetic polymeric thickeners, such as the polyacrylic acid derivatives. Suitable alkanolamides include, but are not limited to, those known in the art of hair care formulations, such as cocamide monoethanolamide (MEA), cocamide diethanolamide (DEA), soyamide DEA, lauramide DEA, oleamide monoisopropylamide (MIPA), stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isosteramide DEA, isostearamide MEA, and combinations thereof.

Fatty alcohols useful in the present formulations are primary or secondary alcohols having about 8 to about 18 carbons, inclusive, either as lauryl alcohol or preferably as a mixture of long-chain lengths, in any combination so long as the mixture includes lauryl alcohol ($C_{12}$) in an amount of at least about 75% by weight, based on the weight of polyethyleneimine in the composition. The fatty alcohols can be straight chain, branched, saturated, and/or unsaturated structures and can be used as $C_{12}$ alone, or as an admixture of $C_{12}$ with any combination of $C_8$–$C_{18}$ fatty alcohols. The preferred fatty alcohols are straight-chained, primary alcohols having about 12 to about 16 carbons, or mixtures of $C_{12}$ with $C_{14}$ and/or $C_{16}$ fatty alcohols. Mixtures of such natural or synthetic fatty alcohols having fatty chain lengths of from about 8 to about 18 carbons, inclusive, are preferred, so long as $C_{12}$ (lauryl alcohol) is included in an amount of at least about 75% by weight, based on the weight of polyethyleneimine included in the composition. Several such mixtures are commercially available and are exemplified by mixtures of such alcohols (including ethoxylated alcohols of the same chain length range), such as ALFONIC 1216 from Vista Chemical Corporation. Other suitable alcohols including the fatty alcohols of the above-described carbon chain lengths which are ethoxylated to contain 1 to about 3, and preferably, an average of 1 or 2 moles of ethylene oxide per mole of fatty alcohol can be used in place of the fatty alcohols themselves. Further, fatty alcohols of other chain lengths can be used in addition to the $C_8$ to $C_{18}$ fatty alcohols so long as, in the preferred embodiment, lauryl alcohol or ethoxylated lauryl alcohol ($C_{12}$) is included in an amount of at least about 75% by weight, based on the weight of PEI in the composition, and the total amount of $C_8$–$C_{18}$ alcohol(s) are present in an amount of at least about 0.5% based on the total weight of the composition. Lower and higher chain length fatty alcohols, e.g., $C_8$, $C_{10}$, $C_{14}$, $C_{16}$ and/or $C_{18}$ fatty alcohols can be included in place of all or a portion of the $C_{12}$ alcohol, but are required in a higher weight ratio of at least about 2.67:1, based on the weight of polyethyleneimine in the composition. Lauryl alcohol, if incorporated as the only fatty alcohol, is only required in an amount of about 75% of the weight of the cationic PEI, although higher relative amounts, including amounts in excess of the weight percentage of cationic PEI, e.g., about 75% to about 200% by weight, also are effective.

Other common cosmetic components and additives can be included in the compositions of the present invention, as long as the basic properties of the hair shampoos and shampoo conditioners are not adversely affected. Such optional cosmetic components and additives include, but are not limited to, nonionic surfactants, amphoteric surfactants, fragrances, dyes, hair colorants, opacifiers, pearlescing agents, thickeners, dandruff-control agents, hydrotropes, foam stabilizers, solubilizers, preservatives, water-softening agents, acids, alkalis, buffers, and the like. These optional components and additives usually are present in weight percentages of less than about 5% by weight each, and usually from about 0.1% to about 20% by weight of the composition in total.

For example, to improve consumer acceptance, both skin mildness and enhanced composition esthetics can be achieved by optionally including polyvinyl pyrrolidone and/or an amphoteric surfactant in the hair shampoo/conditioner in an amount ranging from 0% to about 5% by weight of the composition.

Suitable amphoteric surfactants that can be included in the compositions of the present invention include, but are not limited to, betaines, and hydroxypropylsultaines, or combinations thereof. Examples of amphoteric surfactants include, but are not limited to, cocamidopropyl betaine, lauramidopropyl betaine, coco/oleamidopropyl betaine, coco betaine, oleyl betaine, cocamidopropyl hydroxysultaine, tallow amidopropyl hydroxysultaine and dihydroxyethyl tallow glycinate, or combinations thereof. In general, any amphoteric surfactant can be included in the composition of the present invention as long as the stability, the conditioning, and the cleansing efficiency of the composition are not adversely affected.

The hair shampoo/conditioner compositions of the present invention also can include nonionic surfactants to help impart esthetic, physical, or cleansing properties to the composition. Likewise, the compositions can include other emulsifiers, conditioning agents, inorganic salts, humectants, and similar materials to provide the composition with desirable esthetic or physical properties. Generally, such optional ingredients are present in weight percentages of from about 0% to about 5% each, and from about 0% to about 20% in total, relative to the total weight of the composition.

The carrier of the hair shampoo/conditioner composition of the present invention is predominantly water, but non-aqueous solvents also can be included to help solubilize composition ingredients that are not sufficiently soluble in water, to adjust the viscosity of the composition or to act as a humectant. Suitable solvents include polyols, such as glycerol; glycols, such as ethylene glycol, propylene glycol and hexylene glycol, or mixtures thereof. The optional non-aqueous solvents should not adversely affect the ability of the composition to cleanse and condition the hair or adversely affect consumer appeal of the composition. A non-aqueous solvent can be present in the hair shampoo/conditioner composition of the present invention in an amount ranging from about 0% to about 5% by weight of the composition.

To achieve the full advantage of the present invention, the hair shampoo/conditioner composition is a relatively viscous mixture, e.g., about 3000 to about 8000 centipoises, that is stable indefinitely at temperatures normally found in commercial product storage and shipping. The compositions also have demonstrated sufficient stability to phase separation or precipitation of ingredients at temperatures normally found in commercial product storage and shipping to remain unaffected for periods of one year or more.

The following examples illustrate conditioning shampoos made in accordance with the present invention. It should be understood that the significant figures presented in the example data are not necessarily accurate to three or four significant figures, but, at times, are presented as such to attempt to accurately represent the very small quantities of the dyes included in the compositions, with water quantities calculated after taking into account the small dye quantities. As shown in these examples, the anionic detergent and the cationic polymer (PEI) are stabilized by the lauryl alcohol, so long as it is included in an amount of at least about 75% by weight, based on the weight of the PEI in the composition.

EXAMPLE 1

| Item # | Description | Actual Wt. % |
|---|---|---|
| 1 | SOFT WATER | 73.00 |
| 2 | POLYETHYLENEIMINE 50% (X-LINKED WITH 1,2, DICHLOROETHANE) | 8.00 |
| 3 | DYNOL 120 | 7.00 |
| 4 | LAURYL ALCOHOL | 3.00 |
| 5 | LIQUID CITRIC ACID 50% | 9.00 |

Mixing Procedure Example 1

Add soft water (#1) to the tank. Agitation on moderate.
Add the Polymin P (#2) to the tank. Mix until dissolved.
Add the SLS (#3) to the tank Begin heating to 160°–170° F.
At 150° F. add the lauryl alcohol (#4). Hold at 160°–170° F. for 15 minutes. Stop heating and allow to begin cooling.
Slowly titrate in the citric acid 50% (#5). Mix well.

Comments

During neutralization batch is okay.

It has been found surprisingly and unexpectedly that a relationship exists between the chain length of the fatty alcohol and the resultant stabilization of the anionic/cationic composition. A bell curve exists where lower chain fatty alcohols, $C_8$–$C_{10}$ have less stability than the $C_{12}$ chain length. Greater stability would be expected from $C_{14}$–$C_{18}$ chain lengths and beyond. However, at $C_{18}$, stability is similar to $C_8$ and $C_{10}$ the following examples illustrate this relationship, and the unexpected stability imparted by the $C_{12}$ (lauryl) alcohol.

EXAMPLE 2

Batch was creamy and smooth, however smeared over a watch there were some tiny particles. Overall appearance was good.

| Item # | Description | Actual Wt. % |
|---|---|---|
| 1 | SOFT WATER | 58.00 |
| 2 | POLYMIN P | 1.50 |
| 3 | SLS, 30% | 17.50 |
| 4 | OCTANOL, $C_8$ | 2.00 |
| 5 | ALS, 30% | 17.50 |
| 6 | LIQUID CITRIC ACID 50% | 3.50 |

Mixing Procedure Example 2 ($C_8$, Fatty Alcohol)

Add soft water (#1) to tank. Agitation on moderate.
Add the Polymin P (#2) to tank. Mix until dissolved.
Add the SLS (#3) to the tank. Begin heating to 160°–170° F.
At 150° F. add the octanol (#4). Hold at 160°–170° F. for 15 minutes. Stop heating and allow to begin cooling.
Slowly add the ALS (#5). Mix well.
Slowly titrate in the citric acid 50% (#6). Mix well.

Comments pH=6.0. The solution was slightly opaque without any apparent precipitate. However, after an inspection with a watch glass, there were many very fine particles present. Although there were particles (very fine), the solution could have been used very easily. A mixture of $C_8$ alcohol with $C_{12}$ alcohol would result in no particles.

EXAMPLE 3

Batch was creamy and smooth, however smeared over a watch glass there were some very small particles, smaller than the particles found with the $C_8$ example.

| Item # | Description | Actual Wt. % |
|---|---|---|
| 1 | SOFT WATER | 58.00 |
| 2 | POLYMIN P | 1.50 |
| 3 | SLS, 30% | 17.50 |
| 4 | DECANOL $C_{10}$ | 2.00 |
| 5 | ALS, 30% | 17.50 |
| 6 | LIQUID CITRIC ACID 50% | 3.50 |

Mixing Procedure Example 3

Add soft water (#1) to tank. Agitation on moderate.
Add the Polymin P (#2). Mix until dissolved.
Add the SLS (#3). Begin heating to 160°–170° F.
At 150° F. add the $C_{10}$ alcohol (#4). Hold at 160°–170° F. for 15 minutes. Stop heating and allow to begin cooling.
Slowly add the ALS (#5). Mix well.
Slowly titrate in the citric acid 50% (#6). Mix well.

Comments

After processing the pH=~5.5. The solution was slightly opaque without any apparent precipitate. However, after an inspection with a watch glass, there were many very fine particles present. A mix with $C_{12}$ alcohol would eliminate the fine particles.

EXAMPLE 4

There were no particles present. Smooth and creamy.

| Item # | Description | Actual Wt. % |
|---|---|---|
| 1 | SOFT WATER | 60.10 |
| 2 | POLYETHYLENEIMINE 50% (X-LINKED WITH 1,2 DICHLOROETHANE) | 1.50 |
| 3 | DYNOL 120 | 17.50 |
| 4 | LAURYL ALCOHOL | 2.00 |
| 5 | DYNOL ALS | 17.50 |
| 6 | LIQUID CITRIC ACID 50% | 1.25 |
| 7 | KATHON CG (PRESERVATIVE) | 0.05 |
| 8 | DMDM HYDANTOIN/GLYDANT (PRESERVATIVE) | 0.10 |

Mixing Procedure Example 4

Add the soft water (#1) to the tank. Moderate agitation.
Add the PEI (#2).
Add the SLS (#3). Begin heating to 160°–170° F.
At 150° F. add the lauryl alcohol (#4). Continue heating. After 15 minutes at 160°–170° F. start cooling.
Slowly add the ALS (#5).
Slowly add the citric acid 50% (#6).
At 110° F. add the preservatives (#7 and #8). Mix until uniform.

Comments

After addition of the citric acid 50% there was no precipitation and batch was opaque, homogeneous and thin. After 24 hours, batch was still stable. After 48–72 hours there was some solution separation. Water was separating to the top. When mixed, however, the solution was homogeneous. Even after several days of sitting it would be remixed and there was no precipitate.

EXAMPLE 5

There were no particles present.
Smooth and creamy.

| Item # | Description | Actual Wt. % |
| --- | --- | --- |
| 1 | SOFT WATER | 58.00 |
| 2 | POLYETHYLENEIMINE 50% (X-LINKED WITH 1,2 DICHLOROETHANE) | 1.50 |
| 3 | DYNOL 120 | 17.50 |
| 4 | MYRISTYL ALCOHOL | 2.00 |
| 5 | DYNOL ALS | 17.50 |
| 6 | LIQUID CITRIC ACID 50% | 3.50 |

Mixing Procedure Example 5
  Add soft water (#1) to tank. Agitation on moderate.
  Add the Polymin P (#2). Mix until dissolved.
  Add the SLS (#3). Begin heating to 160°–170° F.
  At 150° F. add the myristyl alcohol (#4). Hold at 170°–180° F. for 15 minutes. Stop heating and allow to begin cooling.
  Slowly add the ALS (#5). Mix well.
  Slowly titrate in the citric acid 50% (#6) Mix well.
Comments
  pH=6.00. The batch was a milky white emulsion without precipitation or particles. Stable with slight agitation once a week.

EXAMPLE 6

There were no particles present. Smooth and creamy.

| Item # | Description | Actual Wt. % |
| --- | --- | --- |
| 1 | SOFT WATER | 58.00 |
| 2 | POLYETHYLENEIMINE 50% (X-LINKED WITH 1,2 DICHLOROETHANE) | 1.50 |
| 3 | DYNOL 120 | 17.50 |
| 4 | CETYL ALCOHOL | 2.00 |
| 5 | DYNOL ALS | 17.50 |
| 6 | LIQUID CITRIC ACID 50% | 3.50 |

Mixing Procedure Example 6
  Add soft water (#1) to tank. Agitation on moderate.
  Add the Polymin P (#2). Mix until dissolved.
  Add the SLS (#3). Begin heating to 160°–170° F.
  At 150° F. add the cetyl alcohol (#4). Hold at 170°–180° F. for 15 minutes. Stop heating and allow to begin cooling.
  Slowly add the ALS (#5). Mix well.
  Slowly titrate in the citric acid 50% (#6) Mix well.
Comments
  After processing pH=6.00 and batch was stable without precipitation. Solution separated slightly but when slightly agitated was homogeneous again. Stable with slight agitation.

EXAMPLE 7

Batch was smooth and creamy, however smeared over a watch glass there were small particles similar to $C_8$–$C_{10}$

| Item # | Description | Actual Wt. % |
| --- | --- | --- |
| 1 | SOFT WATER | 59.75 |
| 2 | POLYETHYLENEIMINE 50% (X-LINKED WITH 1,2 DICHLOROETHANE) | 1.5 |
| 3 | DYNOL 120 | 17.5 |
| 4 | STEARYL ALCOHOL | 2.0 |
| 5 | DYNOL ALS | 17.5 |
| 6 | LIQUID CITRIC ACID 50% | 3.5 |

Mixing Procedure Example 7
  Add the soft water (#1) to the batch with moderate agitation.
  Add the PEI (#2) to the batch.
  Add the SLS (#3) to the batch.
  Begin heating to 170°–180° F.
  At 150° F. add the stearyl alcohol (#4). Continue heating.
  After 30 minutes at 170°–180° F., start cooling.
  Slowly add the ALS (#5) to the batch.
  Slowly add the citric acid (#6) to the batch.
  Mix until uniform.
Comments
  Batch is stable. After 24 hours there was no precipitate.
  The following examples, along with the previous examples, illustrate the practical application of the bell shape curve relationship between the fatty alcohol chain length and stability. In Example 1 a ratio of $C_{12}$ alcohol to PEI of 0.75:1 was necessary for stability. This is the minimum $C_{12}$ alcohol:PEI ratio that provides stability for a PEI-containing conditioning shampoo composition.
  The following Example 8 illustrates well that without a $C_{12}$ fatty alcohol:PEI weight ratio of at least about 0.75, there is instability in the composition.

EXAMPLE 8

| Item # | Description | Actual Wt. % |
| --- | --- | --- |
| 1 | SOFT WATER | 63.10 |
| 2 | POLYETHYLENEIMINE 50% (X-LINKED WITH 1,2 DICHLOROETHANE) | 1.00 |
| 3 | DYNOL 120 | 33.40 |
| 4 | COCAMIDE MEA | 1.00 |
| 5 | LIQUID CITRIC ACID 50% | 1.35 |
| 6 | KATHON CG (PRESERVATIVE) | 0.05 |
| 7 | DMDM HYDANTOIN/GLYDANT (PRESERVATIVE) | 0.10 |

Mixing Procedure Example 8
  Add the soft water (#1) to the tank. Moderate agitation.
  Add the PEI (#2).
  Add the SLS (#3). Begin heating to 160°–170° F.
  At 140° F. add the cocamide MEA (#4). Continue heating.
  After 15 minutes at 160°–170° F. start cooling.
  Add the citric acid 50% (#5).
  At 110° F. add the preservatives (#6 and #7). Mix until uniform.
Comments
  After the addition of citric acid 50% (#5) there was gross precipitation of the PEI (#2). After additional heating beyond 170° F. the precipitate did not solubilize. pH of solution was ≈5.5.

EXAMPLE 9

| Item # | Description | Actual Wt. % |
|---|---|---|
| 1 | SOFT WATER | 63.10 |
| 2 | POLYETHYLENEIMINE 50% (X-LINKED WITH 1,2 DICHLOROETHANE) | 1.10 |
| 3 | DYNOL 120 | 33.40 |
| 4 | GLYCERINE USP | 1.00 |
| 5 | LIQUID CITRIC ACID 50% | 1.25 |
| 6 | KATHON CG (PRESERVATIVE) | 0.05 |
| 7 | DMDM HYDANTOIN/GLYDANT (PRESERVATIVE) | 0.10 |

Mixing Procedure Example 9

Add the soft water (#1) to the tank. Moderate agitation.
Add the PEI (#2).
Add the SLS (#3). Begin heating to 160°–170° F.
At 140° F. add the glycerine USP (#4). Continue heating. After 15 minutes at 160°–170° F. start cooling.
Add the citric acid 50% (#5).
At 110° F. add the preservatives (#6 and #7). Mix until uniform.

Comments

After the addition of the citric acid 50% (#5) there was gross precipitation of the PEI (#2). After additional heating beyond 170° F. the precipitate did not solubilize.

EXAMPLE 10

| Item # | Description | Actual Wt. % |
|---|---|---|
| 1 | SOFT WATER | 63.10 |
| 2 | POLYETHYLENEIMINE 50% (X-LINKED WITH 1,2 DICHLOROETHANE) | 1.10 |
| 3 | DYNOL 120 | 33.40 |
| 4 | POLYSORBATE 20 | 1.00 |
| 5 | LIQUID CITRIC ACID 50% | 1.25 |
| 6 | KATHON CG (PRESERVATIVE) | 0.05 |
| 7 | DMDM HYDANTOIN/GLYDANT (PRESERVATIVE) | 0.10 |

Mixing Procedure Example 10

Add the soft water (#1) to the tank. Moderate agitation.
Add the PEI (#2).
Add the SLS (#3). Begin heating to 140°–150° F.
At 120° F. add the polysorbate 20 (#4). Continue heating. After 15 minutes at 140°–150° F. start cooling.
Add the citric acid 50% (#5).
At 110° F. add the preservatives. Mix until uniform.

Comments

After addition of citric acid (#5) at 150° F. there was gross precipitation. After additional heating up to 175° F., the precipitate did not solubilize.

EXAMPLE 11

| Item # | Description | Actual Wt. % |
|---|---|---|
| 1 | SOFT WATER | 60.10 |
| 2 | POLYETHYLENEIMINE 50% (X-LINKED WITH 1,2 DICHLOROETHANE) | 1.50 |
| 3 | DYNOL 120 | 17.50 |
| 4 | ISODECYL LAURATE | 2.00 |
| 5 | DYNOL ALS | 17.50 |
| 6 | LIQUID CITRIC ACID 50% | 1.25 |
| 7 | KATHON CG (PRESERVATIVE) | 0.05 |
| 8 | DMDM HYDANTOIN/GLYDANT (PRESERVATIVE) | 0.10 |

Mixing Procedure Example 11

Add the soft water (#1) to the tank. Moderate agitation.
Add the PEI (#2).
Add the SLS (#3). Begin heating to 160°–170° F.
At 150° F. add the isodecyl laurate (#4). Continue heating. After 15 minutes at 160°–170° F. start cooling.
Slowly add the ALS (#5).
Slowly add the citric acid 50% (#6).
At 110° F. add the preservatives (#7 and #8). Mix until uniform.

Comments

After addition of the citric acid 50% (#6) there was gross precipitation that did not disappear after continued heating and mixing.

The following Examples 12–14 plus previous examples help illustrate effective ratios of fatty alcohols to PEI for chain lengths higher than $C_{12}$.

At a ratio of 3:4, lauryl alcohol:PEI provides stability, however $C_{14}$, $C_{16}$ or $C_{18}$ fatty alcohols do not. These examples (12–14) had a cottage cheese-like precipitate.

EXAMPLE 12

| Item # | Description | Actual Wt. % |
|---|---|---|
| 1 | SOFT WATER | 56.5 |
| 2 | POLYMIN FG | 2.0 |
| 3 | DYNOL 120 | 17.5 |
| 4 | STEARYL ALCOHOL | 1.5 |
| 5 | SILICONE BLEND (33% GUM/67%% OIL) | 0.5 |
| 6 | DYNOL ALS | 17.5 |
| 7 | LIQUID CITRIC ACID 50% | 4.5 |

Mixing Procedure Example 12

Add the soft water (#1) to the batch with moderate agitation.
Add the PEI (#2) to the batch.
Add the SLS (#3) to the batch. Begin heating to 170°–180° F.
At 150° F. add the stearyl alcohol (#4). Continue heating.
At 170°–180° F. add the silicone blend (#5) with high agitation.
After 30 minutes at 170°–180° F. start cooling.
Slowly add the ALS (#6) to the batch.
Slowly add the citric acid (#7) to the batch.
Mix until uniform.

Comments

Batch precipitated during neutralization at ~pH=8.5.

EXAMPLE 13

| Item # | Description | Actual Wt. % |
|---|---|---|
| 1 | SOFT WATER | 54.5 |
| 2 | POLYETHYLENEIMINE 50% (X-LINKED WITH 1,2 DICHLOROETHANE) | 4.0 |
| 3 | DYNOL 120 | 17.5 |
| 4 | CETYL ALCOHOL | 1.5 |
| 5 | SILICONE BLEND (33% GUM/67% OIL) | 0.5 |
| 6 | DYNOL ALS | 17.5 |
| 7 | LIQUID CITRIC ACID 50% | 4.5 |

Mixing Procedure Example 13

Add the soft water (#1) to the batch with moderate agitation.
Add the PEI (#2) to the batch.
Add the SLS (#3) to the batch. Begin heating to 170°–180° F.
At 150° F. add the cetyl alcohol (#4). Continue heating.
At 170°–180° F. add the silicone blend (#5) with high agitation.
After 30 minutes at 170°–180° F. start cooling.
Slowly add the ALS (#6) to the batch.
Slowly add the citric acid (#7) to the batch.
Mix until uniform.
Comments
During neutralization batch precipitated at ~pH=9.0.

EXAMPLE 14

| Item # | Description | Actual Wt. % |
|---|---|---|
| 1 | SOFT WATER | 54.5 |
| 2 | POLYETHYLENEIMINE 50% (X-LINKED WITH 1,2 DICHLOROETRANE) | 4.0 |
| 3 | DYNOL 120 | 17.5 |
| 4 | STEARYL ALCOHOL | 1.5 |
| 5 | SILICONE BLEND (33% GUM/67% OIL) | 0.5 |
| 6 | DYNOL ALS | 17.5 |
| 7 | LIQUID CITRIC ACID 50% | 4.5 |

Mixing Procedure Example 14

Add the soft water (#1) to the batch with moderate agitation.
Add the PEI (#2) to the batch.
Add the SLS (#3) to the batch.
Begin heating to 170°–180° F.
At 150° F. add the stearyl alcohol (#4). Continue heating.
At 170°–180° F. add the silicone blend (#5) with high agitation.
After 30 minutes at 170°–180° F. start cooling.
Slowly add the ALS (#6) to the batch.
Slowly add the citric acid (#7) to the batch.
Mix until uniform.
Comments
During neutralization batch precipitated at ~pH=9.0.

As illustrated in Examples 5 and 6, at a ratio of 2.67:1 $C_{14}$ and $C_{16}$ are stable. $C_{18}$ (Example 7) at this ratio is marginal and, therefore, it is preferred that the weight ratio of fatty alcohol to polyethyleneimine is at least about 3:1 for $C_8$, $C_{10}$, and $C_{18}$ fatty alcohols.

If a fatty alcohol chain length of $C_8$, $C_{10}$, $C_{14}$, $C_{16}$ or $C_{18}$ is desired, because of opacity or added conditioning benefit, versus $C_{12}$ alcohol, an increase in the fatty alcohol to PEI weight ratio to at least about 2.67:1, preferably at least about 3:1 provides best results.

EXAMPLE 15

| Item # | Description | Actual Wt. % |
|---|---|---|
| 1 | SOFT WATER | 52.60 |
| 2 | POLYETHYLENEIMINE 50% (X-LINKED WITH 1,2 DICHLOROETHANE) | 1.00 |
| 3 | DYNOL 120 | 17.50 |
| 4 | LAURYL ALCOHOL | 10.00 |
| 5 | DYNOL ALS | 17.50 |
| 6 | LIQUID CITRIC ACID 50% | 1.40 |

Mixing Procedure Example 15

Add soft water (#1) to tank. Agitation on moderate.
Add the polymin P (#2) to the tank. Mix until dissolved.
Add the SLS (#3). Begin heating to 160°–170° F.
At 150° F. add the lauryl alcohol (#4). Hold at 160°–170° F. for 15 minutes. Stop heating and allow to begin cooling.
Slowly add the ALS (#5). Mix well.
Slowly titrate in the citric acid 50% (#6). Mix well.
Comments After adding alcohol to the solution, the composition thickened. Neutralized to pH=5.5 w/citric acid, solution thinned out. Solution was without precipitate. Stable at room temperature.

The PEI can be protonated with organic, mineral or strong acids. Previous examples illustrated the use of an organic acid (citric acid). The following examples (16–21) illustrate the use of other acids. In addition, Examples 16–21 illustrate that additional raw materials can be included in a stable composition, such as higher chain length fatty alcohols, ethoxylated fatty alcohols, and additional conditioning agents, such as silicone gums, silicone oils, and blends thereof.

EXAMPLE 16

| Item # | Description | Actual Wt. % |
|---|---|---|
| 1 | SOFT WATER | 28.4794 |
| 2 | DYNOL 120 | 27.5000 |
| 3 | POLYETHYLENEIMINE 50% (X-LINKED WITH 1,2 DICHLOROETHANE) | 3.0000 |
| 4 | COCAMIDE MEA | 2.0000 |
| 5 | LAURYL ALCOHOL | 2.0000 |
| 6 | SILICONE BLEND (33% GUM/67% OIL) | 3.0000 |
| 7 | DISTEARYLDIMONIUM CHLORIDE | 1.5000 |
| 8 | AMMONIUM LAURYL SULFATE, 30% | 27.5000 |
| 9 | HYDROCHLORIC ACID 31% (PH AND PROTONATION OF PEI) | 2.1000 |
| 10 | ISODECYL LAURATE | 2.0000 |
| 11 | FD&C GREEN #3 (10%) | 0.0006 |
| 12 | D&C YELLOW #10 (1%) | 0.1700 |
| 13 | FRAGRANCE PA 70258 | 0.6000 |
| 14 | METHYL & METHYLCHLORO ISOTHIAZOLINONE/K (PRESERVATIVE) | 0.0500 |
| 15 | DMDM HYDANTOIN/GLYDANT (PRESERVATIVE) | 0.1000 |

Mixing Procedure Example 16

Add the soft water (#1) to a compounding tank.

Add sodium lauryl sulfate (#2) to the tank. Agitation on moderate.

Add the polyethyleneimine (#3) to the tank. Mix well. Begin heating to 180°–185° F.

At 150° F. add cocamide MEA (#4). Mix until melted.

At 160° F. add lauryl alcohol (#5). Mix until homogeneous.

At 180° F. add silicone blend (#6) with slightly higher agitation. Mix for 15 minutes.

Add AROSURF TA-100 (#7) with high agitation. Mix for 60 minutes at 180°–185° F. Begin cooling and add the hydrochloric acid 31% (#9). Mix well.

Add the ALS (#8) at a slow rate over a course of 5 minutes. Lower agitation to moderate.

Add isodecyl laurate (#10). Mix until uniform.

At 110° F. add remaining ingredients. Mix until uniform.

Specification pH=5.1

EXAMPLE 17

| Item # | Description | Actual Wt. % |
|---|---|---|
| 1 | SOFT WATER | 60.60 |
| 2 | POLYETHYLENEIMINE 50% (X-LINKED WITH 1,2 DICHLOROETHANE) | 1.50 |
| 3 | DYNOL 120 | 17.50 |
| 4 | LAURYL ALCOHOL | 2.00 |
| 5 | DYNOL ALS | 17.50 |
| 6 | PHOSPHORIC ACID, 85% | 0.90 |

Mixing Procedure Example 17

Add the soft water (#1) to the tank. Moderate agitation. Add the PEI (#2).

Add the SLS (#3). Begin heating to 160°–170° F.

At 150° F. add the lauryl alcohol (#4). Continue heating. After 15 minutes at 160°–170° F. start cooling.

Slowly add the ALS (#5).

Slowly add the phosphoric acid 88% (#6). Mix until uniform.

Comments

Batch was opaque without precipitation or particles. Agitated periodically.

EXAMPLE 18

| Item # | Description | Actual Wt. % |
|---|---|---|
| 1 | SOFT WATER | 59.75 |
| 2 | POLYMIN P | 0.50 |
| 3 | SLS, 30% | 17.50 |
| 4 | MYRISTYL ALCOHOL | 2.67 |
| 5 | UNILIN 350 (PREDOMINANTLY C$_{30}$) | 0.33 |
| 6 | ALS, 30% | 17.50 |
| 7 | LIQUID CITRIC ACID 50% | 1.75 |

Mixing Procedure Example 18

Add soft water (#1) to tank. Agitation on moderate.

Add the Polymin P (#2) to the tank. Mix until dissolved.

Add the SLS (#3) to the tank. Begin heating to 160°–170° F.

At 150° F. add the myristyl alcohol (#4) and Unilin 350 (#5). Hold at 170°–180° F. for 15 minutes. Stop heating and allow to begin cooling.

Slowly add the ALS (#6) to the tank. Mix well.

Slowly titrate in the citric acid 50% (#7). Mix well.

Comments

After processing there were no particles. Batch stable with shaking once a week.

EXAMPLE 19

| Item # | Description | Actual Wt. % |
|---|---|---|
| 1 | SOFT WATER | 60.55 |
| 2 | POLYMIN P | 0.75 |
| 3 | SLS, 30% | 17.50 |
| 4 | MYRISTYL ALCOHOL | 2.67 |
| 5 | C$_{12}$/C$_{16}$ (1 MOLE E.O.) ALCOHOL ETHOXYLATE | 0.33 |
| 6 | ALS, 30% | 17.50 |
| 7 | LIQUID CITRIC ACID 50% | 0.70 |

Mixing Procedure Example 19

Add the soft water (#1) to the tank. Moderate agitation.

Add the PEI (#2) to the tank.

Add the SLS (#3) to the tank. Begin heating to 160°–170° F.

At 150° F. add the myristyl alcohol (#4) and C$_{12}$, C$_{16}$, C$_{22}$ (1 mole e.o.) alcohol ethylate (#5). Continue heating. After 15 minutes at 160°–170° F. start cooling.

Slowly add the ALS (#6) to the tank.

Slowly add the citric acid 50% (#7) to the tank. Mix until uniform.

Comments

After processing batch was stable without any precipitate or particles. Agitated periodically.

EXAMPLE 20

| Item # | Description | Actual Wt. % |
|---|---|---|
| 1 | SOFT WATER | 27.3294 |
| 2 | POLYETHYLENEIMINE 50% (X-LINKED WITH 1,2 DICHLOROETHANE) | 3.0000 |
| 3 | SODIUM LAURYL SULFATE (DYNOL 120, 30% ACTIVE) | 27.5000 |
| 4 | COCAMIDE MEA | 2.0000 |
| 5 | LAURYL ALCOHOL | 2.0000 |
| 6 | SILICONE BLEND (33% GUM/67% OIL) | 3.0000 |
| 7 | DISTEARYLDIMONIUM CHLORIDE | 1.5000 |
| 8 | AMMONIUM LAURYL SULFATE, 30% | 27.5000 |
| 9 | ISODECYL LAURATE (EMOLLIENT) | 2.0000 |
| 10 | LIQUID CITRIC ACID 50% (PH AND PROTONATION OF PEI) | 3.2500 |
| 11 | FD&C GREEN #3 (10%) | 0.0006 |
| 12 | D&C YELLOW #10 (1%) | 0.1700 |
| 13 | FRAGRANCE PA 70258 | 0.6000 |
| 14 | METHYL & METHYLCHLORO ISOTHIAZOLINONE/K (PRESERVATIVE) | 0.0500 |
| 15 | DMDM HYDANTOIN/GLYDANT (PRESERVATIVE) | 0.1000 |

Mixing Procedure Example 20

Add the soft water (#1) to compounding tank.

Add SLS (#3) to the agitation on moderate. Begin heating to 180°–185° F.

Add the polyethyleneimine (#2) to the container.

At 150° F. add cocamide MEA (#4). Mix until melted.

At 160° F. add lauryl alcohol (#5). Mix until homogeneous.

At 180° F. add silicone blend with slightly higher agitation. Mix for 15 minutes.

Add AROSURF TA-100 with high agitation. Mix for 60 minutes at 180°–185° F.

Begin cooling and add ALS at a slow rate over a course of 5 minutes. Lower agitation to moderate.

Add isodecyl laurate. Mix until uniform.

Add citric acid 50%. Mix for 5 minutes.

At 110° F. add remaining ingredients. Mix until uniform.
Specifications

| 1. Property: | pH measurements |
| --- | --- |
| Specification Data: | 5.5–6 |
| | (5.93 observed) |
| 2. Property: | T-SPINDLE VISCOSITY |
| Specification Data at 80° F.: | 20–60 |
| 3. Property: | VISCOSITY |
| Specification Data at 80° F.: | 400–7000 cps. |
| | (observed): pH = 5.93 |
| | Viscosity = 2000 cps. |
| Method of Analysis: | AP#5-0004.02D |

The following Example 21 shows that a composition containing 0.3% stearyl alcohol, 0.6% cetyl alcohol and 2% PEI, as disclosed in Example VI in U.S. Pat. No. 5,104,645, is unstable at the fatty alcohol:PEI ratio of 0.9:2 or 9:20.

EXAMPLE 21

| Item # | Description | Actual Wt. % |
| --- | --- | --- |
| 1 | SOFT WATER | 57.1 |
| 2 | POLYMIN FG* | 2.0 |
| 3 | DYNOL 120 | 17.5 |
| 4 | STEARYL ALCOHOL | 0.3 |
| 5 | CETYL ALCOHOL | 0.6 |
| 6 | SILICONE BLEND (33% GUM/67% OIL) | 0.5 |
| 7 | DYNOL ALS | 17.5 |
| 8 | LIQUID CITRIC ACID 50% | 4.5 |

*Polymin FG (BASF Corporation) Weight average molecular weight ≅ 800

Mixing Procedure Example 21

Add the soft water (#1) to the batch with moderate agitation.

Add the PEI (#2) to the batch.

Add the SLS (#3) to the batch. Begin heating to 170°–180° F.

At 150° F. add the cetyl and stearyl alcohols (#4 and #5) Continue heating.

At 170°–180° F. add the silicone blend (#6) with high agitation.

After 30 minutes at 170°–180° F. start cooling.

Slowly add the ALS (#7) to the batch.

Slowly add the citric acid (#8) to the batch.

Mix until uniform.
Comments

During neutralization batch precipitated at ¯pH=8.5.

The Example VI in U.S. Pat. No. 5,104,645 (Cardin C. W.) was stabilized by 3% ethylene glycol distearate. The ethylene glycol distearate would have opacified the composition and suspended the dandruff active ingredient as well. U.S. Pat. No. 3,400,198 (Lang) also teaches that under pH 10 PEI and anionic detergents are not compatible without a sufficient amount of amphoteric or nonionic detergent. Therefore, it is the suspending agent ethylene glycol distearate that stabilizes Example VI in the '645 patent. An ethylene glycol distearate or other non-fatty alcohol suspending agents are not necessary in accordance with the compositions of the present invention.

What is claimed is:

1. A hair conditioning shampoo composition comprising an emulsion of water; about 5 to about 65 percent by weight of an anionic cleaning surfactant; about 0.01 to about 4 weight percent of a cationic polyethyleneimine, and from about 0.5 to about 10 weight percent of a long-chain fatty alcohol having predominantly about 14 to about 16 carbons in a long chain, wherein the fatty alcohol is included in the composition in an amount of at least about 2.67 times the weight of the polyethyleneimine in the composition; said composition having a pH of about 4 to about 8.

2. The composition of claim 1, wherein the polyethyleneimine is included in an amount of about 0.01% to about 1% by weight.

3. The composition of claim 1, wherein the anionic cleaning surfactant is selected from the group consisting of alkyl sulfates, alkyl sulfonates, alkyl ether sulfates, alkyl ether sulfonates, and mixtures thereof.

4. The composition of claim 1, wherein the cationic polyethyleneimine has a cationic polymer charge density of at least about 10 milliequivalents per gram.

5. The composition of claim 1, wherein the cationic polyethyleneimine has a cationic polymer charge density in the range of about 15 to about 20 milliequivalents per gram.

6. The composition of claim 1, wherein the cationic polyethyleneimine has a weight average molecular weight in the range of about 700 to about 1,000,000.

7. The composition of claim 1, wherein the cationic polyethyleneimine has a weight average molecular weight in the range of about 50,000 to about 1,000,000.

8. A method of shampooing and conditioning hair simultaneously comprising applying to said hair the composition of claim 1.

9. In a hair conditioning shampoo composition containing water; an anionic cleaning surfactant; a long chain fatty alcohol; and a cationic polyethyleneimine; the improvement comprising said fatty alcohol having predominantly about 14 to about 16 carbons in said long chain and being present in the composition in a weight ratio of fatty alcohol to polyethyleneimine of at least 2.67:1.

10. The hair conditioning shampoo composition of claim 9, wherein the weight ratio of the fatty alcohol to polyethyleneimine is at least about 3:1.

11. The composition of claim 9, wherein the cationic polyethyleneimine has a cationic polymer charge density of at least about 10 milliequivalents per gram.

12. The composition of claim 9, wherein the cationic polyethyleneimine has a cationic polymer charge density in the range of about 15 to about 20 milliequivalents per gram.

13. The composition of claim 9, wherein the cationic polyethyleneimine has a weight average molecular weight in the range of about 700 to about 1,000,000.

14. The composition of claim 11, wherein the cationic polyethyleneimine has a weight average molecular weight in the range of about 50,000 to about 1,000,000.

15. A method of shampooing and conditioning hair simultaneously which comprises applying to said hair the composition of claim 9.

* * * * *